(12) United States Patent
Bornhop et al.

(10) Patent No.: US 6,809,828 B2
(45) Date of Patent: *Oct. 26, 2004

(54) UNIVERSAL DETECTOR FOR BIOLOGICAL AND CHEMICAL SEPARATIONS OR ASSAYS USING PLASTIC MICROFLUIDIC DEVICES

(75) Inventors: Darryl J. Bornhop, Lubbock, TX (US); Kelly Swinney, Martinsville, VA (US); Dmitry Markov, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/053,877

(22) Filed: Jan. 24, 2002

(65) Prior Publication Data

US 2002/0135772 A1 Sep. 26, 2002

Related U.S. Application Data

(60) Provisional application No. 60/263,760, filed on Jan. 25, 2001.

(51) Int. Cl.[7] .............................................. G01B 9/02
(52) U.S. Cl. ....................................................... 356/517
(58) Field of Search ................................. 356/481, 517

(56) References Cited

U.S. PATENT DOCUMENTS

| | | |
|---|---|---|
| 4,660,974 A | 4/1987 | Machler et al. |
| 4,908,112 A | 3/1990 | Pace |
| 4,950,074 A | 8/1990 | Fabricius et al. |
| 5,073,024 A | 12/1991 | Valette et al. |
| 5,108,179 A | 4/1992 | Myers |
| 5,120,131 A | 6/1992 | Lukosz |
| 5,125,740 A | 6/1992 | Sato et al. |
| 5,165,005 A | 11/1992 | Klainer et al. |
| 5,173,747 A | 12/1992 | Boiarski et al. |
| 5,215,883 A | 6/1993 | Chu |
| 5,273,633 A | 12/1993 | Wang |
| 5,305,071 A | 4/1994 | Wyatt |
| 5,325,170 A * | 6/1994 | Bornhop ..................... 356/128 |
| 5,377,008 A | 12/1994 | Ridgway |
| 5,633,708 A | 5/1997 | Svendsen |

(List continued on next page.)

OTHER PUBLICATIONS

Kelly Swinney et al., ""Micro–interferometric Backscatter Detection Using a Laser Diode"," Analytica Chimica Acta, p. 265–280, (Sep. 22, 1999).

(List continued on next page.)

*Primary Examiner*—Frank G. Font
*Assistant Examiner*—Patrick Connolly
(74) *Attorney, Agent, or Firm*—Jones, Tullar & Cooper, PC

(57) ABSTRACT

An on-chip interferometric backscatter detector (OCIBD) makes use of plastic substrates in which a rectangular sample channel is formed. While any plastic material can be used to form the channel substrate, the substrate is most preferably formed from polydimethylsiloxane (PDMS). An incident laser beam reflects off of the sample channel walls and through the sample in the channel, thereby generating backscattered reflections that create interference fringe patterns. The fringe patterns are detected by a photodetector and used to determine various properties of the sample. To provide the best results, the laser beam diameter should be no smaller than the channel width so that the entire channel will be illuminated by the beam, and preferably should be slightly, e.g., 5%, larger. This will insure that the laser light reflected off of the walls of the channel will generate the desired interference fringe patterns, despite the less than optimum rectangular geometry of the channel walls. A reference channel can be provided to improve the accuracy of the measurements made with the detector. One notable application of the invention is the analysis of binding experiments on biochemical functional species, such as proteins and DNA.

27 Claims, 5 Drawing Sheets

U.S. PATENT DOCUMENTS

| | | | |
|---|---|---|---|
| 5,636,017 | A | 6/1997 | Bruno et al. |
| 5,663,790 | A | 9/1997 | Ekstrom et al. |
| 5,694,210 | A | 12/1997 | Newell et al. |
| 5,740,291 | A | 4/1998 | De Lasa et al. |
| 5,770,029 | A | 6/1998 | Nelson et al. |
| 5,815,258 | A | 9/1998 | Nakanishi |
| 5,824,204 | A | 10/1998 | Jerman |
| 5,841,914 | A | 11/1998 | Shieh et al. |
| 5,846,708 | A | 12/1998 | Hollis et al. |
| 5,852,495 | A | 12/1998 | Parce |
| 5,867,266 | A | 2/1999 | Craighead |
| 6,381,025 | B1 * | 4/2002 | Bornhop et al. ............ 356/517 |

OTHER PUBLICATIONS

Kelly Swinney et al., ""Ion Analysis Using Capillary Electrophoresis with Refractive Index Detection"," Microchemical Journal, p. 154–163, (Sep. 22, 1999).

Yolanda Fintschenko et al., "Silicon Microtechnology and Microstructures in Separation Science," Journal of Chromatography, vol. A (No. 819), p. 3–12, (Sep. 22, 1998).

E.F. Schipper et al., ""The Waveguide Mach–Zender Interferometer as Atrazine Sensor"," Analytical Chemistry 1998, p. 1192–1197, (Mar. 15, 1998).

Yanzhuo Deng et al., ""On–column Refractive–index Detection Based on Retroreflected Beam for Capillary Electrophoresis"," Applied Optics, vol. 37 (No. 6), p. 998–1005, (Feb. 20, 1998).

Norbert Burggraft et al., ""Holographic Refractive Index Detector for Application in Microship–based Separation Systems"," Analyst, p. 1443–1447, (Jul. 22, 1998).

G.J. Veldhuis et al., ""Highly–sensitive Passive Integrated Optical Spiral–Shaped Waveguide Refractometer"," Applied Physics Letters, vol. 71, (No. 20), p. 2895–2897, (Nov. 17, 1997).

Christopher K. Kenmore et al., ""Refractive–index Detection by Interferometric Backscatter in Packed–capillary High–Performance Liquid Chromatography"," Journal of Chromatography, vol. A (No. 762), p. 219–225, (Sep. 22, 1997).

Darryl J. Bornhop et al., ""Polarimetry in Capillary Dimensions", " Analytical Chemistry, vol. 68 (No. 10), p. 1677–1684, (May 15, 1996).

Darryl J. Bornhop et al., ""Microvolume Index of Refraction Determinations by Interferometric Backscatter"," Applied Optics, vol. 34 (No. 18), p. 3234–3239, (Jun. 20, 1995).

Joseph C. StClaire, "Heat Index Flow Monitoring in Capillaries with Interferometric Backscatter Detection," Analytical Chemistry, vol. 72 (No. 19), p. 4726–4730, (Oct. 1, 2000).

Kelly Swinney et al., "Ultrasmall Volume Refractive Index Detection Using Microinterferometry," Review of Scientific Instruments, vol. 71, No. 7, pp. 2684–2692 (Jul. 2000).

* cited by examiner

UNIVERSAL DETECTOR FOR BIOLOGICAL AND CHEMICAL SEPARATIONS OR ASSAYS USING PLASTIC MICROFLUIDIC DEVICES

PRIORITY CLAIM UNDER 35 U.S.C. 119(e)

This application claims the benefit, under 35 U.S.C. § 119(e), of U.S. Provisional Application No. 60/263,760, filed Jan. 25, 2001.

BACKGROUND OF THE INVENTION

1. Field of the Invention

The present invention relates to a sensitive and simple optical detection scheme, for on-chip, high sensitivity universal (refractive index) solute detection for molded plastic microfluidic systems. This detector, based on micro-interferometry, allows for picoliter detection volumes and universal analyte detection, a task not previously possible in plastic microfluidic devices. The detection system has numerous applications, including universal/RI detection for CE (capillary electrophoresis), CEC (capillary electrochromatography) and FIA, physiometry, cell sorting/detection by scatter, ultra micro calorimetry, flow rate and temperature sensing. Because the detector has universal response the technique is also well suited to proteomics efforts where label free protein and DNA assays are needed. Thus, the invention allows the target molecules to be studied in their native state without additional chemical derivation.

2. Description of the Background Art

The ability to perform sensitive, universal, non-invasive, nano-scale sensing is imperative. Many applications exist, including flow or velocity sensing, universal solute detection, calorimetry, time resolved enthalpies and antigen-antibody binding, where non-invasive, sub-nano-volume detection is not only desired but essential. The area of miniaturized total analysis systems is driven by the need to analyze large numbers of samples quickly. For example, tens of millions of samples have been and must be analyzed by electrophoresis in order to map the human genome. Other areas where microfabricated instrumentation would decrease analysis time and accelerate progress include the high-throughput screening of combinatorial libraries to aid in drug discovery, the development of a library of genetic fingerprints for the members of the U.S. military and the screening of blood samples for infectious disease. Recently it has been shown that Surface Plasmon Resonance (SPR) technique can be applied, with limited success, to some of the aforementioned tasks. Even though SPR can be used for label free molecule detection, its drawbacks include the necessity of using expensive gold-plated substrates (problematic for plastics) and high quality optical prisms for surface illumination. It addition, it has a complicated flow-cell designs for sample delivery and only works when the solute is within nanometers of the gold surface.

Interferometry is among one of the most sensitive optical detection techniques known and as such, the most promising refractive index (universal) measurement techniques alternative to SPR when probing of nano-scale environments is necessary. One of the most promising techniques for on-chip interferometric detection is disclosed in Applicants' copending application, U.S. patent application Ser. No. 09/519,860, filed Mar. 6, 2000. The '860 application discloses an on-chip interferometric backscatter detector (OCIBD), which employs a channel of capillary dimensions that is preferably etched in a substrate for reception of a sample to be analyzed. A laser source generates an easy to align, simple optical train comprised of an unfocused laser beam that is incident on the etched channel for generating the backscattered light. The backscattered light comprises interference fringe patterns that result from the reflective and refractive interaction of the incident laser beam with the channel walls and the sample. These fringe patterns include a plurality of light bands whose positions shift as the refractive index of the sample is varied, either through compositional changes or through temperature changes, for example. A photodetector detects the backscattered light and converts it into intensity signals that vary as the positions of the light bands in the fringe patterns shift, and can thus be employed to determine the refractive index (RI), or an RI related characteristic property, of the sample. Preferably, the etched channel has a generally hemispherical cross sectional shape. A unique multi-pass optical configuration is inherently created by the channel characteristics, and is based on the interaction of the unfocused laser beam and the curved surface of the channel, that allows interferometric measurements in small volumes at high sensitivity.

One of the challenges encountered in the development of the OCIBD disclosed in the '860 application lies in the fabrication of the micro-capillary channels in the substrate. In one preferred embodiment, the substrate is formed from glass or silica. There are several reasons why glass and silica-based substrates were initially chosen. First, etched channels in such substrates can be fabricated by modifying the well-known procedures used by the electronics industry to manufacture silicon chips. Second, these substrates are optically transparent allowing the use of previously developed detection methodology. Third, like fused silica capillaries used in capillary electrophoresis, these substrates have charged silanol groups on their surface and thus are capable of generating electroosmotic flow, the most common form of fluid transport in microfabricated devices. Fourth, these substrates possess high bulk resistivity and dielectric breakdown field strengths allowing the high electrical field strengths, commonly used in capillary electrophoresis, to be applied across micro-fabricated channels filled with a low-conductivity buffer. Fifth, there exists a large number of surface modification procedures commonly used in separation science that are easily adapted to planar chips made of glass, silica or silicon.

Although great success has been achieved with glass chips, there are several additional requirements or limitations involved with their use that make them less desirable than other material substrates. First, all fabrication steps must be carried out under clean room conditions adding considerable overhead cost to the production of microfabricated instrumentation. Second, the masks that are used in the photolithography process are very expensive. Third, these devices are typically sealed by high temperature annealing requiring temperatures of up to 1000° C., a process which is not trivial, is labor intensive and often produces low device yields. Fourth and finally, glass, silica or silicon based microfluidic devices are brittle and fragile, making them hard to work with and less robust.

SUMMARY OF THE INVENTION

To address the limitations of using silica or glass substrates, the present invention provides an on-chip interferometric backscatter detector that makes use of plastic substrates in which rectangular channels are formed. Surprisingly, even though one might initially assume that a rectangular channel would not be the proper geometry to provide the requisite backscattered reflections to generate the desired fringe patterns, the inventors have discovered that the system of the '860 application works equally well when the hemispherical etched channel is replaced by a rectangular channel formed in plastic.

The use of plastics is advantageous because they are considerably cheaper and require less fabrication time than glass/silica/silicon substrates. For example, the time required to design and produce a new device in plastic can be done in a week at a cost of $100-$200 while producing microchannels in glass or silica can take several months and cost as much as several thousand dollars. Other attributes of using plastics are that high geometrical aspect ratios (nearly vertical walls) are obtainable, little to no clean room time is required, high temperature sealing processes are not necessary, conventional detection methodologies are compatible, and the resulting devices are cheap enough to be considered disposable. The use of a rectangular channel also greatly simplifies fabrication of he device as compared to that of a semi cylindrical channel.

While any plastic material can be used to form the channel substrate, the substrate is most preferably formed from polydimethylsiloxane (PDMS). PDMS as a substrate has become popular in the last few years for several reasons. First, it is extremely economical and microfabricated structures can be produced quickly. Second, PDMS is optically transparent at visible wavelengths and low in background fluorescence making conventional detection methodologies compatible. Third, it is chemically and physically inert. Fourth, it is electrically insulating allowing electrophoresis systems to be fabricated.

The rectangular channels are preferably formed in the substrate using a molding or other suitable technique. The dimensions of the channels can be varied over a wide range, and are limited primarily by the width of the incident laser beam. In particular, to provide the best results, the laser beam diameter should be no smaller than the channel width so that the entire channel will be illuminated by the beam, and preferably should be slightly, e.g., 5%, larger. This will insure that the laser light reflected off of the walls of the channel will generate the desired interference fringe patterns, despite the less than optimum rectangular geometry of the channel walls. To provide an acceptable device resolution, the laser beam diameter should not be too large, and should thus be limited to approximately 2 mm. The depth of the channel is also preferably, though not necessarily, larger than its width, say by 50% or more. However, this does not affect device performance and is selected rather to further simplify fabrication of the channel.

In the preferred embodiment, an optional reference channel is also employed to improve the accuracy of the resulting sample measurements made with the OCIBD. The two channels are located in close proximity of each other and are illuminated by the laser beam, either simultaneously or sequentially (in near-real-time). By monitoring position changes for both of the resulting fringe patterns, it is possible to discriminate the desired RI signal generated by the sample from the background. These background interferences can be produced by gradients flowing through the channels and/or by environmental perturbations such as temperature and pressure changes. Using the sample and reference configuration also allows accurate temperature compensation. Implementation of the reference channel and successful compensation of RI gradients will make the OCIBD insensitive to RI changes other than those due to the target compound in the sample channel and will facilitate reaction dynamics to be monitored in real-time with flowing systems. Ultimately using a sample-reference approach to OCIBD will lead to substantially improved signal-to-noise ratio (S/N) for the OCIBD system.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE PREFERRED EMBODIMENT

Figure 1:
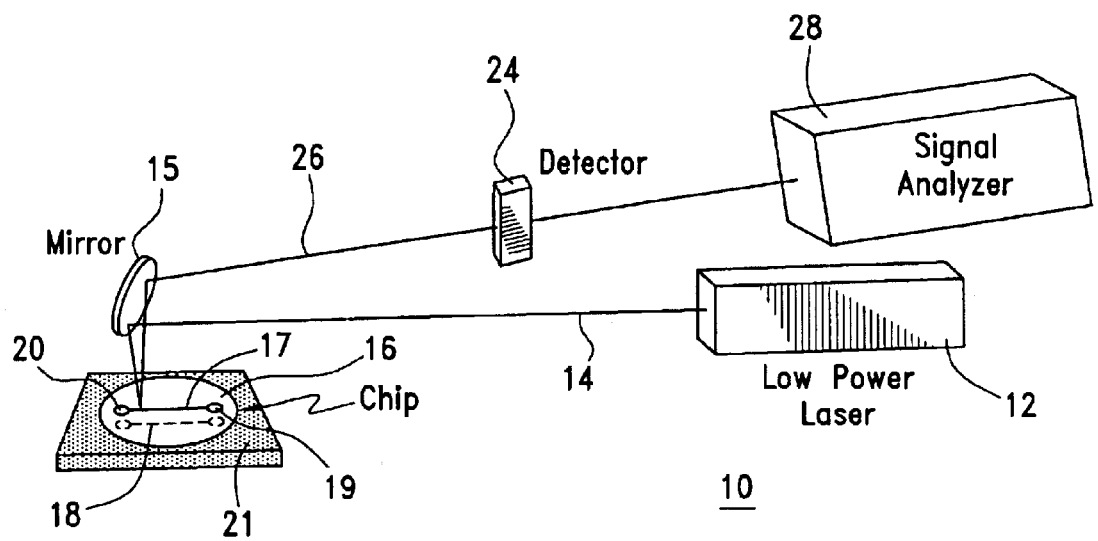
FIG. 1 is a schematic block diagram of an on-chip interferometric backscatter detector (OCIBD) that is constructed in accordance with a preferred embodiment of the present invention.

A block diagram of an on-chip interferometric backscatter detector (OCIBD) 10 that is constructed in accordance with a preferred embodiment of the present invention and uses rectangular channels in plastics is illustrated in FIG. 1. The OCIBD 10 is essentially the same as the arrangement used with etched channels in silica as disclosed in the previously mentioned U.S. application Ser. No. 09/519,860, which is hereby incorporated by reference. In addition, the OCIBD 10 makes use of a technique that employs backscattered light to determine the RI or RI related characteristic properties of a sample. The backscatter detection technique is generally disclosed in U.S. Pat. No. 5,325,170 to Bornhop, which is also hereby incorporated by reference. However, in the present invention where backscatter detection is used for "on-chip" detection with ultra-small sample volumes, the technique employed is referred to as Micro-Interferometric Backscatter Detection or MIBD.

The detector 10 includes a laser or other source of coherent light 12, which is preferably a low power (3–15 mW) laser (He/Ne or Diode), and generates a spatially and temporally coherent beam 14, the diameter of which should preferably be no greater than about 2 mm to insure good detection resolution. As with any interferometric technique for micro-chemical analysis, MIBD benefits from many of advantages lasers provide, including high spatial coherence, monochromaticity, and high photon flux. The intensity of the laser beam can be reduced as needed with a series of optional neutral density filters. Upon reduction of the intensity, the beam 14 is directed to an optional mirror 15 that re-directs the beam onto a plastic substrate chip 16 having a sample channel 17 of rectangular cross section formed therein for reception of a sample volume to be analyzed. An optional second, reference channel 18, also having a rectangular cross section and discussed in greater detail below, can be provided for reference purposes as illustrated by the dashed lines in FIG. 1.

The chip 16 can be formed from any suitable plastic material, however, it is preferably formed from polydimethylsiloxane (PDMS) for the reasons discussed previously. Acrylic is another example of a material that can be used for the chip 16, but it is not as easy to work with as PDMS.

Figure 2:
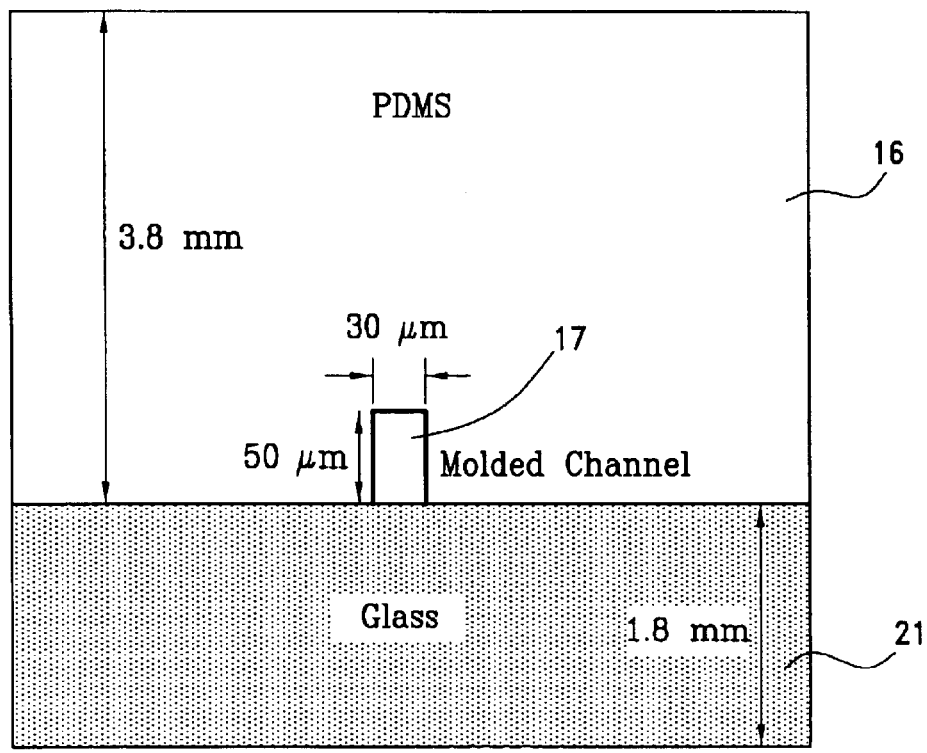
FIG. 2 is an end view of a cross section of the OCIBD of FIG. 1 showing the molded sample channel in a PDMS substrate with a glass plate adhered thereto.

Formed in the chip 16 at the ends of the sample channel 17 are first and second ports 19 and 20 for introduction and removal of sample from the OCIBD 10. The unaltered laser beam 14 is allowed to impinge onto the channel 17 at a distance that is about 1 mm from the exit port 20. With reference to the end-on view of FIG. 2, the substrate chip 16 is preferably covered with a glass plate 21 that is pressed together with the plastic chip 16 and remains intact due to adhesion. In one experiment, the glass plate was selected to be 1.8 mm thick and the molded PDMS chip 16 was selected to be 3.8 mm thick In the example embodiment of FIG. 2, the cross section of the channel 17 itself takes on the form of a rectangle having a depth of 50 $\mu$m and a width of 30 $\mu$m, although rectangles of other dimensions will of course work, including equal sided rectangles, i.e., squares, for example. It is preferred that the width of the sample channel 17 not exceed the diameter of the laser beam 14 (e.g., 2 mm or less), and preferably should be 95% or less the laser beam diameter to insure that the beam 14 will fully illuminate the channel 17. This helps insure that acceptable fringe patterns will be generated by the interfering reflections of the laser beam 14 off of the sample channel walls and through a sample in the sample channel 17. Surprisingly, under these conditions, the rectangular channel 17 produced a unique multi-pass optical configuration much like that observed with the half-cylinder shaped etched channels in silica as disclosed in the '860 application. As with the silica chips, when an unfocused laser beam was allowed to impinge on a rectangular channel after passing through 3.75 mm of PDMS, an interference pattern was produced and detected in the direct backscatter.

Returning now to FIG. 1, a photodetector 24 receives the backscattered reflections 26 from the sample in the sample channel 17, and can be one of any number of image sensing devices, including a bi-cell position sensor, a CCD camera and laser beam analyzer assembly, a slit-photodetector assembly, an avalanche photodiode, or any other suitable photodetection device. The backscattered light 26 comprises interference fringe patterns that result from the reflective and refractive interaction of the incident laser beam 14 with the walls of the channel 17 and the sample contained therein. These fringe patterns include a plurality of light bands (see FIG. 4) whose positions shift as the refractive index of the sample is varied, either through compositional changes or through temperature changes, for example. The photodetector 24 detects the backscattered light 26 and converts it into one or more intensity signals that vary as the positions of the light bands in the fringe patterns shift. For fringe profiling, the photodetector 24 is preferably mounted above the chip 16 at an approximately 45° angle thereto. The intensity signals from the photodetector 24 are fed into a signal analyzer 28 for fringe pattern analysis, and determination there from of the RI or an RI related characteristic property of a sample in the sample channel 17.

As discussed previously, the embodiment of FIG. 1 can also employ an optional reference channel 18. In this variation, the two channels 17 and 18 are located in close proximity of each other and are both illuminated by the laser beam 14, either simultaneously or sequentially (in near-real-time). The sample channel 17 would then receive the sample to undergo some type reaction to be monitored, while the reference channel 18 would receive a reference sample that would only be exposed to effects of background interference. By monitoring position changes for both of the resulting fringe patterns, it is possible to discriminate the desired RI signal generated by the sample from the background. These background interferences can be produced by gradients flowing through the channels 17 and 18 and/or by environmental perturbations such as temperature and pressure changes. Using the sample and reference configuration of FIG. 1 will also allow accurate temperature compensation. Implementation of the reference channel 18 and successful compensation of RI gradients will make the OCIBD 10 insensitive to RI changes other than those due to the target compound in the sample channel 17 and will facilitate reaction dynamics to be monitored in real-time with flowing systems. Ultimately using a sample-reference approach to OCIBD will lead to substantially improved signal-to-noise ratio (S/N) for the OCIBD system.

There are several methods that can be used to fabricate the rectangular channels 17 and 18 in the plastic substrate chip 16 including casting, injection molding, laser ablation, machining operations or imprinting methods. In one preferred molding method for use with PDMS-based chips, a negative chrome mask containing the desired channel features is first created. Next, a silicon wafer is spin coated with negative photoresist, e.g. SU-8 50 (where "50" denotes film thickness at 3000 rpm and can be varied depending on particular device designs), and baked. Then, the coated wafer is exposed to UV light through the negative chrome mask and rebaked. Following the second bake, the wafer is developed using propylene glycol methyl ether acetate creating a positive master. The master is then silanized by placing it in a desiccator under vacuum for 1 hour with a vial containing tridecafluoro-1,1,2,2-tetrahydrooctyl-1-trichlorosilane (not critical but a very useful step). A degassed 10:1 mixture of PDMS oligomer and crosslinking agent is then poured onto the master and allowed to cure for 4 hour at 65° C. The PDMS is then removed from the mold yielding a pattern of negative relief channels. Channel reservoirs are created using a hole punch. Following a short plasma oxidation step the PDMS substrate is then reversibly bonded to a glass plate by first cleaning both substrates (PDMS and glass) with isopropyl alcohol, drying under a stream of $N_2$, and pressing the two plates together to remove air bubbles. Depending on application and particular chip requirements, the PDMS substrate can be also sealed with a glass or plastic plate or another piece of PDMS.

In experiments on the invention, it was shown for the first time that on-chip RI detection could be performed with molded rectangular channels in PDMS. Using a simple optical train consisting of the molded rectangular channel 17, the laser 12 and the photodetector 24, it was shown that the OCIBD 10 could be used to detect solutes at the micromolar level (38 femtomoles/3.5 picograms) in just 112 picoliters. Further, it was demonstrated that the response of the detector 24 to changes in RI is linear (>2.5 decades in concentration) and highly reproducible.

Figure 3:
FIG. 3 is a gray scale reconstruction of the backscatter interference pattern produced from the interaction of an unconditioned laser beam with a molded rectangular channel in PDMS.
Figure 4:
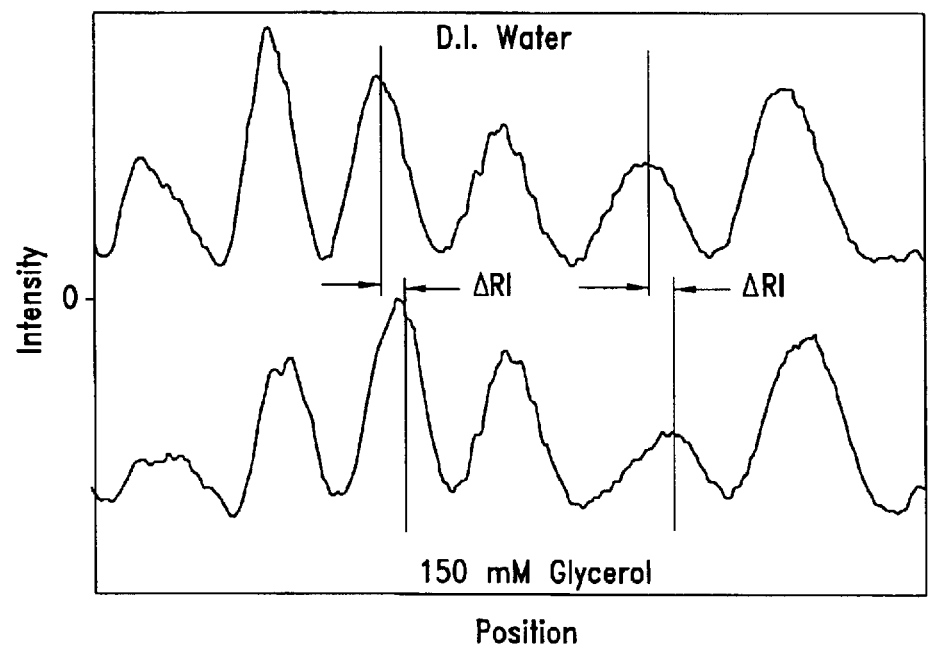
FIG. 4 is a graph of the response of the backscatter interference pattern to changes in the RI of the fluid within the probe volume for the PDMS chip.

The gray scale image shown in FIG. 3 depicts the profile of an interference pattern produced from a rectangular channel filled with distilled/deionized water (black represents no photons and white denotes detector saturation). Even though the channel has the general shape of a rectangle with no curved surfaces, high contrast interference fringes somewhat similar to those seen with the isotropically etched channels in silica were observed. Drawing on previous research with the OCIBD (etched channels) and MIBD (full capillaries), it was postulated that positional changes in the backscatter fringe pattern would be observed upon changing the refractive index of the fluid contained within the probe volume. FIG. 4 is a line profile of two fringe patterns: one when water was in the channel and one when 150 mM glycerol was present. This figure illustrates the OCIBD response, showing that the position of the backscatter fringes shift significantly (169 $\mu$m/mRIU), as the refractive index or the fluid in the channel is changed (water to 150-mM glycerol).

These observations are important for several reasons. First, the features on the chip 16 that produce the interference fringes are very easy and inexpensive to manufacture since PDMS can be purchased for a nominal price and little to no clean room time is required for microfabrication. Second, as with the isotropically etched silica chips, no additional optics are needed in order to generate the fringe pattern. Third and finally, the fringes that are produced from a rectangular sample channel 17 molded in PDMS are very high contrast implying interferometry with high finesse, leading to sensitive detection of optical pathlength changes.

A simple way to quantitatively evaluate the refractive index sensitivity of on-chip interferometric backscatter is with a position sensor such as a CCD camera in communication with a laser beam analyzer (LBA). The advantage of position measurements based on array detection is that they are inherently insensitive to the non-uniformities in the intensity profile of a single fringe. Further, fringe movement can be tracked over large distances facilitating enhanced operating dynamic range because detection is not limited by the width and slope of the fringe. In the experiments, positional measurements were obtained by employing a 9-micron pixel CCD camera (COHU) based laser beam analyzer system (LBA) (Spiricon). The centroid determination function of the LBA, which works by locating the X-Y coordinate pair that corresponds to the center of the backscatter fringe of interest, was used to measure/quantify the positional shifts of the imaged fringe pattern. All fringe shift measurements were determined relative to the initial position of the fringe for the blank solution.

Figure 5:
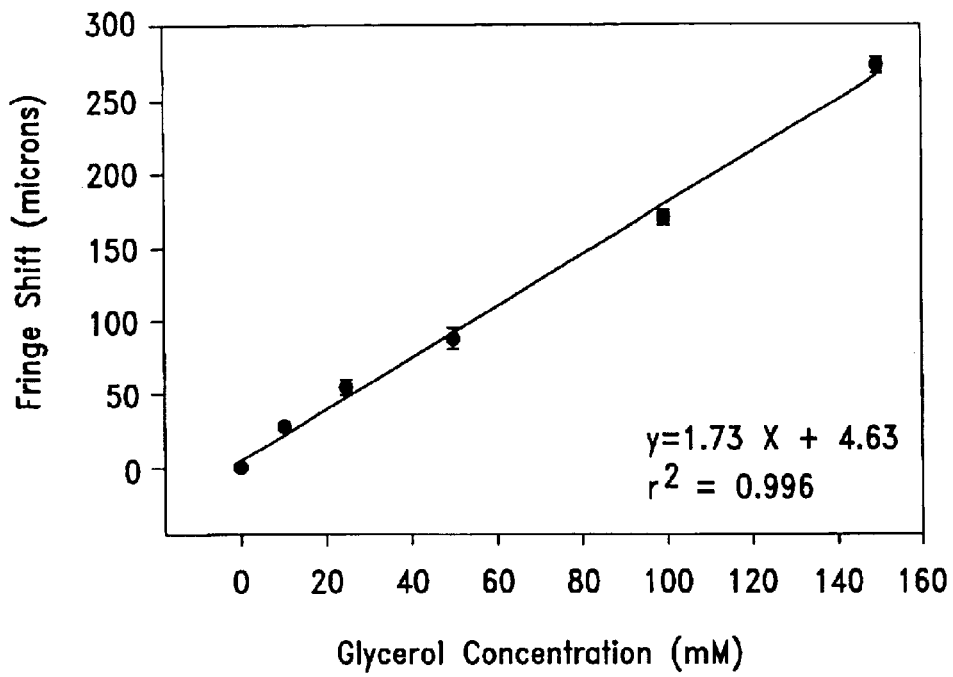
FIG. 5 is a graph showing the calibration curve in triplicate of fringe shift versus glycerol concentration for PDMS chips using a ccd-lba system.

In this configuration, the CCD camera was mounted approximately 28 cm from the front surface of the chip 16 such that the fringe pattern could be imaged. A calibration curve of fringe position versus glycerol concentration (0–150 mM) was generated using a 75 micron diameter beam of the diode laser and the CCD/LBA assembly to determine the RI sensitivity of OCIBD with PDMS chips (FIG. 5) under static conditions. A linear relationship ($r^2$= 0.996) exists between solute concentration and relative positional shift of the selected backscatter fringe ($3^{rd}$ fringe from centroid) for a concentration range of 2.5 decades and is highly reproducible (STD=±4.5 microns). The $3\sigma$ mass limit of detection OCIBD with molded channels in PDMS was calculated and determined to be 0.58 pmole or 53.6 pg (5.2 mM) using a 112 pL probe volume. A corresponding $\Delta n=6.8\times10^{-5}$ RIU was quantifiable at the 99.9% confidence level.

The RI sensitivity of the device using CCD-LBA detection is limited by the low resolution of the CCD imager integrating software. In this setup, the sensitivity of the system to positional shifts of the fringe pattern is limited to 9 microns. Regardless the LBA does allow convenient analysis of the fringes and evaluation of their movement in response to changes in refractive index when refractive index changes greater than the detection limit ($\Delta n=6.8\times10^{-5}$ RIU) are produced.

Figure 6:
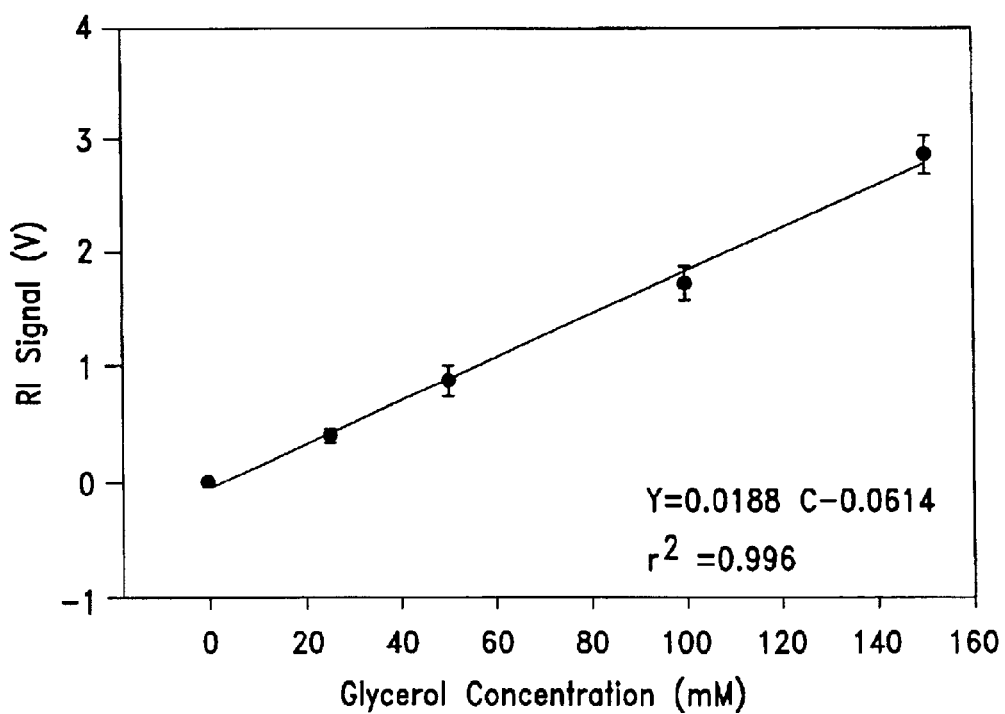
FIG. 6 is a graph showing the calibration curve in triplicate of RI signal versus glycerol concentration for the PDMS chip using an apd detector.

These preliminary results suggest that OCIBD can function as an analytically useful detection methodology with molded channels of rectangular shape in plastics, however the need to improve the S/N of the measurement is clear. Since the smallest positional shift that can be detector by the CCD-LBA system is about 9 microns, in order for the S/N ratio of the system to increase, a detector capable of sensing smaller positional changes is required. It has previously been shown with OCIBD and etched channels in silica, that a solid state photodetector such as an avalanche photodiode can be used to increase the S/N ratio of the system and thus improve performance. Thus, the CCD-LBA detection system was replaced with the small area (0.3 mm diameter) avalanche photodiode capable of detecting a change in fringe position of about 1 micron. The APD was aligned on the edge of the interrogated fringe ($3^{rd}$ from the centroid) and in a similar procedure as that used with the CCD-LBA system, a calibration curve of intensity versus glycerol concentration was generated (FIG. 6). Positional changes in the backscatter fringe pattern were quantifiable as intensity changes and linear with variations in solute concentration (refractive index). In fact, the calibration curve was linear ($r^2$=0.996) over a 2.5 decade concentration range and reproducible from run to run for triplicate determinations. The calculated $3\sigma$ detection limits for OCIBD with PDMS rectangular channels, with an APD and a 75 micron diameter beam from a diode laser, was 638 $\mu$M. In the detector volume of 112 pL and at the detection limit, there was 71 fmole or 6.6 pg of glycerol. At the detection limit, a change in refractive index of $8.32\times10^{-6}$ was detectable at the 99.9% confidence level and corresponds to an improvement of 8.2 times over the detection limits obtained with the CCD-LBA system. While further improvements in detection limits are desired, this simple technique has concentration detection limits that are analytically useful (58.7 ppm).

In conclusion, the inventors have discovered and demonstrated for the first time that refractive index measurements can be performed directly on-chip with molded rectangular shaped channels in plastic. Using the simple optical configuration based on backscattering interferometry with a 30 $\mu$m by 50 $\mu$m rectangular channel in PDMS and an avalanche photodiode detection scheme, changes in refractive index of $8.32\times10^{-6}$ RIU can be sensed at the 99.9% confidence level. This change in refractive index corresponds to a $3\sigma$ mass detection limit of $38\times10^{-15}$ mole or $3.5\times10^{-12}$ g ($638\times10^{-6}$ M) for glycerol in a $112\times10^{-12}$ L probe volume. However, the interferometric backscatter detector proposed here is robust, functions on the nano-scale (picoliter volumes) can be used to perform universal solute detection at the femtomole level and is scalable. In addition, the device can be used to perform non-invasive thermometry in picoliter volumes, subsequently allowing velocity measurements to done on fluids in nanostructures. Using this simple device, fundamental investigations into joule heating produced in on-chip CE have been completed. It should even be possible to perform calorimetry, measure the heat of mixing, monitor enzyme reactions, and do time resolved enthalpies determinations. The invention can be used to study antigen-antibody binding, perform biochemical assays, and study receptor-ligand interactions. Further, the inventors have recently been able to successfully use surface immobilization techniques to modify the surface of PDMS micro-fluidic channels with 'receptors' and monitor ligand binding by quantifying the shift in the OCIBD fringe pattern. As little as, 45.8 femtomol of biotin could be detected after irreversible binding to surface-bound streptavidin, a detection limit comparable to those previously published.

Figure 7:
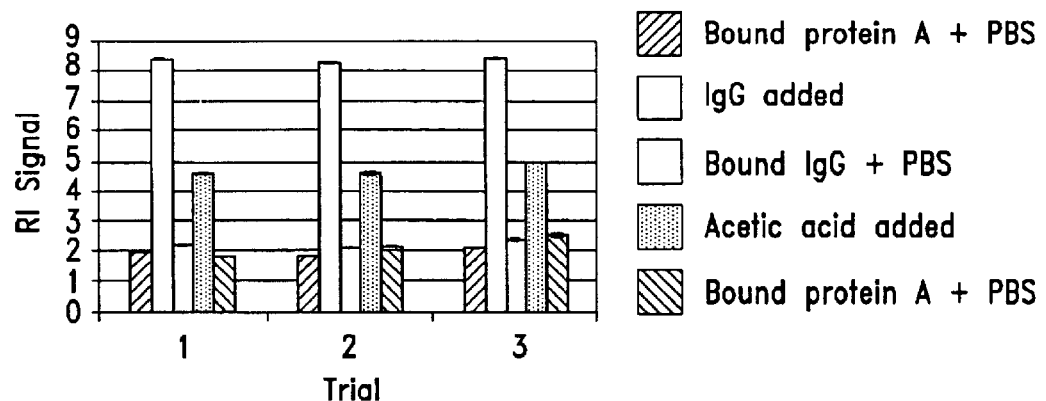
FIG. 7 is a bar graph showing the RI signal for a number of Protein A-IgG binding experiments using an OCIBD constructed in accordance with the present invention.

Furthermore, an OCIBD constructed in accordance with the preferred embodiment can and has been used to monitor binding of various biochemical functional species, such as complimentary strands of DNA, complimentary proteins and antibody antigen pairs. In a first study, the reversible binding of Human IgG fragment C to biotinalyted Protein A immobilized on the surface of the rectangular microfluidic channel was monitored. The results of this study are shown in FIG. 7. If there was 50% coverage of the surface and Human IgG has a spheroid dimension (3 nm×15 nm), the mass detection limits of $4.5 \times 10^{-15}$ mol of Human IgG ($F_c$) bound to Protein A was achieved. In addition, no signal was observed by OCIBD when IgG F(ab')$_2$ fragment was introduced to the channel as expected since Protein A does not bind to IgG F(ab')$_2$.

Figure 8:
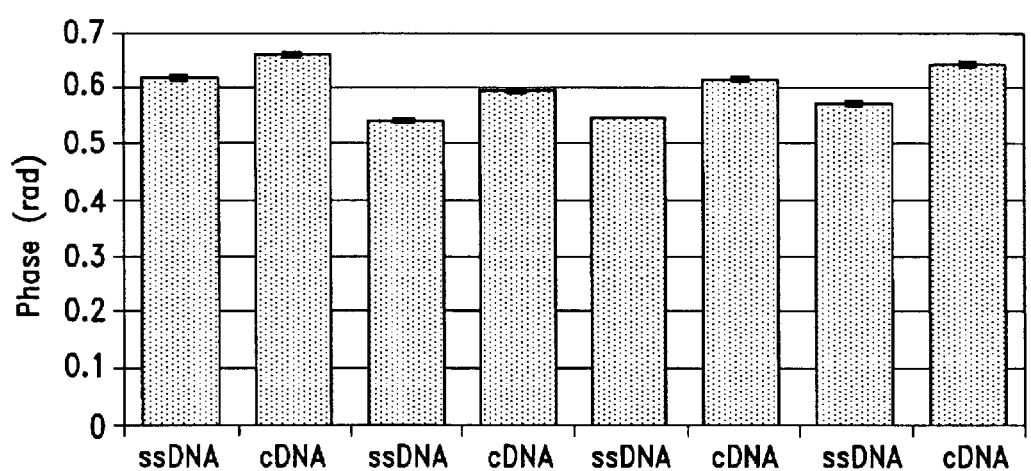
FIG. 8 is a bar graph showing the change in absolute signal for mouse Actin DNA hybridization reactions using an OCIBD constructed in accordance with the present invention: ssDNA corresponds to a single strand DNA immobilized on the surface and PBS buffer present in the channel; cDNA corresponds to complete hybridization reaction when ssDNA and its complimentary cDNA are on the surface and PBS buffer is in the channel.
Figure 9:
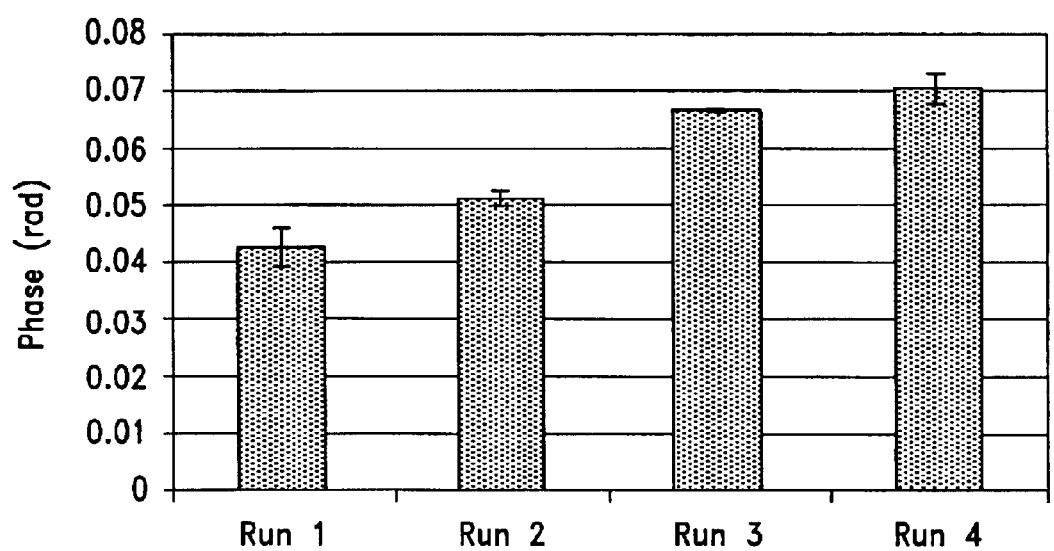
FIG. 9 is a bar graph showing the change in the signal produced by repetitive hybridization and denaturation of mouse Actin DNA molecules immobilized on the surface. Variation in the signal between runs can be attributed to incomplete cDNA removal.

OCIBD also allows label-free analysis of hybridization reactions such as DNA—DNA binding reactions to be performed. Hybridization of single stranded DNA (ssDNA) to its complimentary strand (cDNA) were performed in 50 $\mu$m×50 $\mu$m rectangular microfluidic channels molded in PDMS in the probe volume of $2.5 \times 10^{-10}$ L. The mouse Actin ssDNA surface immobilization was performed in three steps: first a photoactive form of biotin was deposited onto channel walls and activated with UV light; then avidin was introduced into the channel and allowed to react with immobilized photobiotin; next injected biotinalated ssDNA was allowed to react with the immobilized avidin. A 2048-element array in combination with Fourier analysis was used to quantify the positional change of the fringe pattern. The change in absolute signal due to hybridization and denaturization is shown in FIG. 8. Using the single-channel configuration of OCIBD and when reaction kinetics are not desired, the signal is recorded in two stages: a) when only ssDNA present on the channel surface and the fluid within the channel is the PBS buffer; and b) after the introduced cDNA strand has fully reacted with the immobilized ssDNA strand and after the PBS buffer has been reintroduced into the channel. This approach allows for the elimination of erroneous results due to bulk RI changes from the target species solution. From the signal magnitude of a determination, he analytical utility is demonstrated with a simple calculation. Using the parameters: Avidin dimensions of 5.6×5 nm, a probe volume of $2.5 \times 10^{-10}$ L, Avogadro's number, and based on the worst-case scenario assumption that 100% of the surface is covered with avidin and 100% of it is reacted with ssDNA $1.2 \times 10^{-16}$ mol (12 fmol) of bound DNA can be reliably detected. As shown in FIG. 9 this determination gives a result with a relatively large signal to noise (S/N) ratio. Further interrogation of the data suggests the S/N=13, so the 3σ detection limits would be 3 fmol of target DNA reacting with its counter part. These results represent an approximately two-decade improvement over SPR.

Finally, previous evidence from modeling and empirical tests indicates OCIBD performance is insensitive to the dimensions of the microfluidic channel in which the sample is contained. Thus, reduction of the channel to the sub-micron regime is predicted to be feasible. It is also expected that OCIBD is applicable to universal analyte nanosensing applications such as non-invasive thermometry, solute—solute binding and fluidics based separations, label-free reaction monitoring. To date, no universal, optical detector has been put forth that is capable of sensing concentration, temperature, density or pressure changes of samples contained within molded rectangular microfluidic channels in plastics.

The invention also finds use as a detector for other chip-scale analytical schemes including electrophoresis, $\mu$-HPLC separations and FIA. It is possible to detect molecules important to cellular function, high throughput analysis, and pharmaceutical screening. The interferometer can also be used in biochemical assays and to quantify environmental analytes. It is also possible to perform microthermometry, the device has the capability of measuring small temperature changes [in the $10^{-3°}$ C. range] allowing for cellular respiration, protein folding, calorimetry, and fundamental chemical binding studies to be performed in picoliter volumes. Furthermore, when using special surface chemistry to selectively bind solutes, such as DNA oligiomers or antibodies, without sacrificing specificity/sensitivity. Use of the device to perform flow sensing, pressure sensing, time resolved enthalpies and perform detection for products eluted from focusing techniques such as flow cytometry is also viable, as well as ability to monitor label-free reactions and to quantify the interference brought on by fluorescent markers normally attached to biomolecules.

Although the invention has been disclosed in terms of a preferred embodiment and variations thereon, it will be understood that numerous additional variations and modifications could be made thereto without departing from the scope of the invention as defined in the following claims.

What is claimed is:

1. An interferometric detection system comprising:
   a) a plastic substrate;
   b) a first rectangular channel formed in said substrate for reception of a liquid sample to be analyzed;
   c) a coherent light source for generating a coherent light beam, said light source being positioned to direct said light beam into said channel to thereby generate backscattered light comprising interference fringe patterns, said fringe patterns including a plurality of spaced light bands whose positions shift in response to changes in the refractive index of said liquid sample; and
   d) a photodetector for receiving said backscattered light and generating one or more intensity signals that vary as a function of positional shifts of said light bands.

2. The interferometric detection system of claim 1, wherein said substrate is formed from PDMS.

3. The interferometric detection system of claim 1, wherein said laser beam is selected to have a diameter of 2 mm or less.

4. The interferometric detection system of claim 3, wherein said channel has a width that is no larger than said diameter of said laser beam.

5. The interferometric detection system of claim 1, further including a second rectangular channel formed in said substrate, said second channel acting as a reference channel for detection and compensation of background interference.

6. A method for determining a characteristic of a sample comprising the steps of:
   a) providing an interferometric detection system comprising:
      1) a plastic substrate;
      2) a first rectangular channel formed in said substrate for reception of a liquid sample to be analyzed;

3) a coherent light source for generating a coherent light beam, said light source being positioned to direct said light beam into said channel to thereby generate backscattered light comprising interference fringe patterns, said fringe patterns including a plurality of spaced light bands whose positions shift in response to changes in the refractive index of said liquid sample; and 4) a photodetector for receiving said backscattered light and generating one or more intensity signals that vary as a function of positional shifts of said light bands;

b) introducing a sample to be analyzed into said first rectangular channel; and c) determining a characteristic of said sample by analyzing said one or more intensity signals generated by said photodetector when said sample is in said channel.

7. The method of claim 6, wherein said characteristic to be determined is whether first and second biochemical functional species bind with one another, and said step of introducing a sample to be analyzed into said first rectangular channel comprise introducing said first biochemical functional species into said channel and then introducing said second biochemical functional species into said channel to facilitate a binding reaction between said first and second biochemical species.

8. The method of claim 7, wherein said first and second biochemical functional species are selected from the group comprising complimentary strands of DNA, complimentary proteins and antibody antigen pairs.

9. The method of claim 6, wherein said substrate is selected to be formed from PDMS.

10. The method of claim 6, wherein said laser beam is selected to have a diameter of 2 mm or less.

11. The method of claim 10, wherein said channel is selected to have a width that is no larger than said diameter of said laser beam.

12. The method of claim 6, wherein a second rectangular channel is formed in said substrate and said method further comprise the steps of introducing a reference sample in said second rectangular channel, determining a characteristic of said reference sample by analyzing said one or more intensity signals generated by said photodetector when said reference sample is in said second rectangular channel; and, employing said characteristic of said reference sample to compensate for background interference effects in the determination of said characteristic of said sample in said first channel.

13. An interferometric detection system comprising:

a) a substrate;

b) a first channel formed in said substrate for reception of a liquid sample to be analyzed;

c) a coherent light source for generating a coherent light beam, said light source being positioned to direct said light beam into said channel to thereby generate backscattered light comprising interference fringe patterns, said fringe patterns including a plurality of spaced light bands whose positions shift in response to changes in the refractive index of said liquid sample; and d) a photodetector for receiving said backscattered light and generating one or more intensity signals that vary as a function of positional shifts of said light bands.

14. The interferometric detection system of claim 13, wherein said substrate is formed from PDMS.

15. The interferometric detection system of claim 13, wherein said laser beam is selected to have a diameter of 2 mm or less.

16. The interferometric detection system of claim 15, wherein said channel has a width that is no larger than said diameter of said laser beam.

17. The interferometric detection system of claim 13, further including a second channel formed in said substrate, said second channel acting as a reference channel for detection and compensation of background interference.

18. A method for determining a characteristic of a sample comprising the steps of:

a) providing an interferometric detection system comprising:

1) a substrate;

2) a first channel formed in said substrate for reception of a liquid sample to be analyzed;

3) a coherent light source for generating a coherent light beam, said light source being positioned to direct said light beam into said channel to thereby generate backscattered light comprising interference fringe patterns, said fringe patterns including a plurality of spaced light bands whose positions shift in response to changes in the refractive index of said liquid sample; and 4) a photodectector for receiving said backscattered light and generating one or more intensity signals that vary as a function of positional shifts of said light bands;

b) introducing a sample to be analyzed into said first channel; and c) determining a characteristic of said sample by analyizing said one or more intensity signals generated by said photodetector when said sample is in said channel.

19. The method of claim 18, wherein said characteristic to be determined is whether first and second biochemical functional species bind with one another, and said step of introducing a sample to be analyzed into said first channel comprises introducing said first and second biochemical functional species into said channel to facilitate a binding reaction between said first and second biochemical species.

20. The method of claim 19, wherein said first and second biochemical functional species are selected from the group comprising complimentary strands of DNA, complimentary proteins and antibody antigen pairs.

21. The method of claim 18, wherein said characteristic to be determined is whether a ligand in said sample binds with one or more receptors.

22. The method of claim 21, wherein said receptors are immobilized in said channel.

23. The method of claim 18, wherein said characteristic to be determined is a label-free analysis of a hybridization reaction in said channel.

24. The method of claim 18, wherein said substrate is selected to be formed from PDMS.

25. The method of claim 18, wherein said laser beam is selected to have a diameter of 2 mm or less.

26. The method of claim 25, wherein said channel is selected to have a width that is no larger than said diameter of said laser beam.

27. The method of claim 18, wherein a second channel is formed in said substrate and said method further comprise the steps of introducing a reference sample in said second channel, determining a characteristic of said reference sample by analyzing said one or more intensity signals generated by said photodetector when said reference sample is in said second channel; and, employing said characteristic of said reference sample to compensate for background interference effects in the determination of said characteristic of said sample in said first channel.

* * * * *